(12) United States Patent
Ornan et al.

(10) Patent No.: US 7,417,044 B2
(45) Date of Patent: Aug. 26, 2008

(54) TADALAFIL HAVING A LARGE PARTICLE SIZE AND A PROCESS FOR PREPARATION THEREOF

(75) Inventors: Inbal Ornan, Arad (IL); Ehud Amir, Ramat-Aviv (IL); Guy Samburski, Ganot-Hadar (IL); Yhoshoa Ovadya, Migdal Haemek (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 294 days.

(21) Appl. No.: 11/364,630

(22) Filed: Feb. 27, 2006

(65) Prior Publication Data

US 2006/0286166 A1 Dec. 21, 2006

Related U.S. Application Data

(60) Provisional application No. 60/656,664, filed on Feb. 25, 2005, provisional application No. 60/683,058, filed on May 19, 2005, provisional application No. 60/736,807, filed on Nov. 14, 2005, provisional application No. 60/737,080, filed on Nov. 15, 2005, provisional application No. 60/677,514, filed on May 3, 2005, provisional application No. 60/733,012, filed on Nov. 2, 2005, provisional application No. 60/748,341, filed on Dec. 6, 2005.

(51) Int. Cl.
| | |
|---|---|
| *A01N 43/58* | (2006.01) |
| *A01N 43/60* | (2006.01) |
| *A61K 31/50* | (2006.01) |
| *A61K 31/495* | (2006.01) |
| *C07D 241/36* | (2006.01) |

(52) U.S. Cl. ...................................... 514/249; 544/343
(58) Field of Classification Search ................ 544/343; 514/249
See application file for complete search history.

(56) References Cited

U.S. PATENT DOCUMENTS

| | | | |
|---|---|---|---|
| 5,859,006 | A | 1/1999 | Daugan |
| 5,985,326 | A | 11/1999 | Butler |
| 6,821,975 | B1 | 11/2004 | Anderson et al. |

FOREIGN PATENT DOCUMENTS

| | | | |
|---|---|---|---|
| WO | WO 95/19978 | A1 | 7/1995 |
| WO | WO 96/38131 | A1 | 12/1996 |
| WO | WO 2004/011463 | A1 | 3/2004 |
| WO | WO 2005/068464 | A2 | 7/2005 |
| WO | WO 2005/116030 | A1 | 12/2005 |
| WO | WO 2006/050458 | A2 | 5/2006 |

*Primary Examiner*—Zachary C Tucker
(74) *Attorney, Agent, or Firm*—Kenyon & Kenyon LLP

(57) ABSTRACT

The present invention provides particulate tadalafil having a particle size of about 200 to about 600 microns and a process for controlling the particle size of tadalafil.

29 Claims, No Drawings

TADALAFIL HAVING A LARGE PARTICLE SIZE AND A PROCESS FOR PREPARATION THEREOF

RELATED APPLICATIONS

This application claims the benefit of U.S. Provisional Application No. 60/733,012, filed Nov. 2, 2005; U.S. Provisional Application No. 60/748,341, filed Dec. 6, 2005; U.S. Provisional Application No. 60/656,664, filed Feb. 25, 2005; U.S. Provisional Application No. 60/736,807, filed Nov. 14, 2005; U.S. Provisional Application No. 60/737,080, filed Nov. 15, 2005; U.S. Provisional Application No. 60/683,058, filed May 19, 2005; and U.S. Provisional Application No. 60/677,514, filed May 3, 2005. The contents of these applications is incorporated by reference.

FIELD OF THE INVENTION

The invention is directed to particulate tadalafil having a particle size of about 200 microns to about 600 microns and a process for the preparation thereof.

BACKGROUND OF THE INVENTION (6R-trans)-6-(1,3-benzodioxol-5-yl)-2,3,6,7,12,12a-hexahydro-2-methyl-pyrazino[1',2':1,6]pyrido[3,4-b]indole-1,4-dione (tadalafil) having the formula

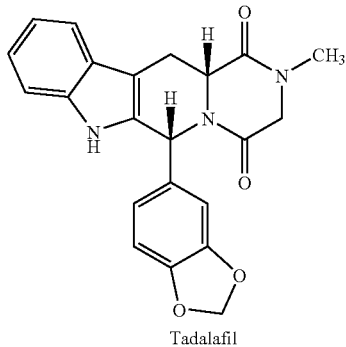

Tadalafil is a potent and selective inhibitor of the cyclic guanosine monophosphate (cGMP)—specific phosphodiesterase enzyme PDE5. The inhibition of PDE5 increases the amount of cGMP, resulting in smooth muscle relaxation and increased blood flow. Tadalafil is therefore currently used in the treatment of male erectile dysfunction.

The solid state physical properties of an active pharmaceutical ingredient (API), such as tadalafil, can be very important in formulating a drug substance and can have profound effects on the ease and reproducibility of formulation. Particle size, for example, may effect the flowability and mixability of a drug substance. Small particles are also filtered and washed more slowly during isolation processes, and thus may increase the time and expense of manufacturing a drug formulation.

U.S. Pat. No. 5,859,006 discloses the synthesis of tadalafil. U.S. Pat. No. 6,821,975 describes the synthesis of tadalafil wherein 90% of the particles have a particle size of less than about 40 microns and a pharmaceutical composition containing this particle size.

There is a need in the art for tadalafil having a large particle size and for a process for the preparation thereof.

SUMMARY OF THE INVENTION

In one aspect, the present invention provides particulate tadalafil wherein at least 90% of the particles, by volume, have a particle size of about 200 to about 600 microns.

In another aspect the present invention provides a process of preparing particulate tadalafil wherein at least 90% of the particles have a particle size of about 200 to about 600 microns including the steps of:

(a) combining tadalafil with a solvent selected from the group consisting of $C_3$-$C_8$ ketones, aliphatic nitriles, lower aliphatic alcohols, water and mixtures thereof, to obtain a slurry;

(b) heating the slurry of step (a) to a temperature of about 45° C. to about reflux to obtain a clear solution;

(c) combining the solution of step (b) with water to obtain a suspension; and (d) recovering particulate tadalafil wherein at least 90% of the particles have a particle size of about 200 to about 600 microns.

In yet another aspect, the present invention provides a process for controlling the particle size of tadalafil including the steps of:

(a) providing particulate tadalafil wherein at least 90% of the particles have a particle size of about 200 to about 600 microns; and (b) milling the tadalafil of step (a) to obtain tadalafil having a desired particle size.

In a further aspect, the present invention provides pharmaceutical compositions including tadalafil prepared according to processes of the present invention in any of its embodiments and one or more pharmaceutically acceptable excipients, diluents or carriers.

In another aspect, the present invention provides a process for preparing a pharmaceutical formulation including mixing tadalafil prepared according to processes of the present invention and a pharmaceutically acceptable carrier.

DETAILED DESCRIPTION OF THE INVENTION

The present invention provides particulate tadalafil wherein at least 90% of the particles, by volume, have a particle size of about 200 to about 600 microns.

Tadalafil having a large particle size, such as that described above, may be filtered off and dried easily. Large particle size tadalafil allows the preparation of a final product containing less residual solvent and water.

The invention provides a process for preparing particulate tadalafil wherein at least 90% of the particles have a particle size of about 200 to about 600 microns. The process of the invention allows the dissolution rate of the tadalafil to be controlled. Processing tadalafil to bring the particle size within a particular narrow range can also enhance manufacturing capability, allowing the preparation of pharmaceutical compositions that exhibit an improved bioavailability of tadalafil. Tadalafil of the present invention is thus well suited for formulations.

"Particulate tadalafil" refers to tadalafil in powder or granular form comprised of a plurality of discrete particles, or individual units of mass. The individual particles of the particulate tadalafil of the present invention can be regular-shaped, or they can have an irregular shape. When the particles have an irregular shape, nominal size of a particle refers to the dimension of the so-called equivalent sphere, a concept known in the field of particle size analysis.

The individual particles of a sample or aliquot of the solid particulate tadalafil of the present invention are not of uniform size. Rather, a sample or aliquot of a solid particulate tadalafil of the present invention is comprised of particles of different sizes that can be size-classified or distributed in an array of discrete, adjacent intervals of particle size. If the size of the intervals is small enough, the array of particle sized approaches a continuum of particle sizes. This collection of discrete particle size intervals together with their population is referred to as the particle size distribution (PSD).

Measurement and characterization of particle size distributions is known in the art. It is possible to compare samples of particulate tadalafil on the basis of individual points on a cumulative particle size distribution curve. The measurements are represented as d(0.X)=Y (where X and Y are Arabic numerals), each "d" describing an individual point on a cumulative PSD curve. The number "X" represents the percentage (number, volume, or weight) of particles in the population having a nominal size up to and including "Y". Thus, d(0.9)=250μ is characteristic of a PSD in which 90% (number, volume, or weight) of the particles in a population have a nominal size of about 250μ or less (at least some particles having a nominal dimension of 250μ) and so forth. When PSD is determined by the well-know laser-diffraction method described herein, the d(0.X) measurement depicts a volume average.

The skilled artisan knows that the results of PSD determination by one technique can be correlated with that from another technique on an empirical basis by routine experimentation.

The process of the invention for preparing particulate tadalafil, wherein at least 90% of the particles have a particle size of about 200 to about 600 microns, includes the steps of:

(a) combining tadalafil with a solvent selected from the group consisting of $C_3$-$C_8$ ketones, nitriles, lower aliphatic alcohols, water and mixtures thereof to obtain a slurry;

(b) heating the slurry of step (a) to a temperature of about 45° C. to about reflux to obtain a clear solution;

(c) combining the solution of step (b) with water to obtain a suspension; and (d) recovering particulate tadalafil wherein at least 90% of the particles have a particle size of about 200 to about 600 microns.

Tadalafil suitable for use in step (a) can be obtained by combining a solution of TDCl in a solvent selected from the group consisting of aromatic hydrocarbons, lower aliphatic alcohols, and alkyl esters of lower carboxylic acids, with methylamine to form a reaction mixture, and heating the reaction mixture at a temperature of about 20° C. below reflux to about reflux temperature of the solvent for about 1 hour to about 48 hours, as disclosed in co-pending United States Application Ser. No. 11/364,598. Alternatively, tadalafil can be obtained by any other process known to one skilled in the art.

$C_3$-$C_8$ ketones useful as solvents in step (a) include acetone, methylisobutyl ketone (MIBK) and methylethyl ketone (MEK).

The term "nitrites" refers to a compound having the formula: R—CN wherein R represents a $C_1$ to $C_6$ alkyl group, preferably a $C_1$ to $C_3$ alkyl group. A particularly preferred nitrile solvent is acetonitrile.

The term "lower aliphatic alcohols," as used herein, refers to organic compounds having the general structure R—OH, wherein R is a linear or branched $C_1$-$C_6$ alkyl group. Lower aliphatic alcohols that are preferred for use in the process of the invention include methanol, ethanol, iso-propanol and butanol.

Preferred solvents in step (a) include acetone and mixtures of $C_3$-$C_8$ ketones or nitrites with water or lower aliphatic alcohols. More preferably, the solvent in step (a) is a mixture of at least one $C_3$-$C_8$ ketone and water; most preferably, the solvent is a mixture of acetone and water. The ratio of $C_3$-$C_8$ ketone or nitrile to water or lower aliphatic alcohol used in step (a) is about 2:1 to about 10:1.

Preferably, the slurry of step (a) includes about 2.5% to about 4.5% of tadalafil, by volume. Preferably, the slurry is heated to a temperature of about 45° C. to about 100° C., more preferably to about 45° C. to about 65° C. to obtain a clear solution. The solution preferably does not contain undissolved tadalafil.

The solution obtained in step (b) can be filtered, if desired, to dispose of foreign particles, such as dust and active carbon, while maintaining the filtered solution and filtrate at almost the same temperature. If the solution is filtered, the temperature is preferably maintained at a temperature such that the tadalafil remains dissolved in the solution to be filtered. Preferably the temperature is maintained at about 45° C. to about 65° C.

The solution of step (b) is preferably cooled to a temperature of about 60° C. to about 30° C. prior to combining the solution with water.

The solution is combined with an amount of water equaling about 1 to about 3 times the volume of the solvent used in step (a). The amount of water used is preferably about 2 times the volume of solvent used in step (a).

The manner of combining the solution and water effects the size of the crystal nuclei that are formed. While combining the solution and water, a substantially constant temperature is maintained and localized high concentrations of tadalafil are avoided or quickly dissipated. In this manner, applicants can best control the resulting particle size of tadalafil. The solution and water are thus combined in small aliquots or portionwise. Preferably, they are combined in a drop-wise manner, such as by adding water to the solution in a drop-wise manner. The solution and water can be combined over a period of about 30 minutes to about 15 hours, more preferably, for about 1 hour to about 5 hours. Most preferably, the solution and water are combined over a period of about 3.5 hours to about 4 hours.

Particulate tadalafil wherein at least 90% of the particles have a particle size of about 200 to about 600 microns can be recovered from the suspension by methods known in the art. For example, the suspension can be cooled to a temperature of about 50° C. to about 20° C. over about 30 minutes to about 24 hours, preferably over about 3.5 hours. The suspension can then be filtered, preferably in a centrifuge, and optionally, can be washed with water.

Optionally, seeding the hot solution with tadalafil may be performed after step (b).

Heating the suspension obtained in step (c) to a temperature of about 45° C. to about reflux leads to dissolution of tadalafil having a small particle size, while tadalafil particles of larger size remain un-dissolved. Subsequent cooling of the suspension induces crystallization of the new larger particle size tadalafil on the existing tadalafil precipitate. Preferably, the suspension is cooled for about 1 hour to about 6.5 hours, more preferably, for about 4 hours to about 5 hours.

Thus, prior to the recovery of tadalafil in step (d), the suspension obtained in step (c) can optionally be heated and subsequently cooled repeatedly until the desired particle size is obtained.

The process of the present invention can be performed on an industrial scale.

Tadalafil having a large particle size, such as about 200 microns to about 600 microns, can be milled to tadalafil having a smaller particle size in a milling process that is adapted to the desired particle size. Thus, the milling process provides control over the obtained particle size of tadalafil. For example, milling can be performed by a cone mill, which operates by breaking particles with an impeller that revolves within a conical perforated screen. There is a narrow gap of about 0.025" between the impeller and the screen. The material to be milled is fed to the mill by either manual feeding, a mechanical feeder (such as a screw feeder or a vibratory feeder) or by pneumatic conveying. The particles of the material hit the rotating impeller, and are attrited between the screen and the impeller. The milled particles exit the mill through the perforated holes and are either collected in a closed container attached to the mill discharge or conveyed by vacuum to a collector. The particle size of the product can be controlled by either changing the rotating speed of the impeller, selection of screens with different hole sizes, or using different types of impellers.

The present invention provides a process for controlling the particle size of tadalafil to obtain tadalafil having a desired particle size comprising the steps of:

(a) providing particulate tadalafil wherein at least 90% of the particles have a particle size of about 200 to about 600 microns; and (b) milling the tadalafil of step (a) to obtain tadalafil having a desired particle size of about 40-100 microns.

The present invention also provides a process for controlling the particle size of tadalafil to obtain tadalafil having a desired particle size comprising the steps of:

(a) combining tadalafil with a solvent selected from the group consisting of $C_3$-$C_8$ ketones, nitrites, lower aliphatic alcohols, water and mixtures thereof to obtain a slurry;

(b) heating the slurry of step (a) to a temperature of about 45° C. to about reflux to obtain a clear solution;

(c) combining the solution of step (b) with water to obtain a suspension;

(d) recovering particulate tadalafil wherein at least 90% of the particles have a particle size of about 200 to about 600 microns; and (e) milling the tadalafil of step (d) to obtain tadalafil having a predetermined particle size of about 40-100 microns.

The invention provides pharmaceutical compositions comprising particulate tadalafil prepared according to processes of the present invention and one or more pharmaceutically acceptable excipients, diluents or carriers.

The invention also encompasses methods of making a pharmaceutical formulation that includes combining tadalafil and a pharmaceutically acceptable excipient. As used herein, the term "pharmaceutical formulation" includes tablets, pills, powders, liquids, suspensions, solutions, emulsions, granules, capsules, suppositories, or injection preparations.

As used herein, the term "pharmaceutical composition" includes tablets, pills, powders, liquids, suspensions, emulsions, granules, capsules, suppositories, or injection preparations. Pharmaceutical compositions containing the tadalafil of the present invention may be prepared by using diluents or excipients such as fillers, bulking agents, binders, wetting agents, disintegrating agents, surface active agents, and lubricants. Various modes of administration of the pharmaceutical compositions of the invention can be selected depending on the therapeutic purpose, for example tablets, pills, powders, liquids, suspensions, emulsions, granules, capsules, suppositories, or injection preparations.

Any excipient commonly known and used widely in the art can be used in the pharmaceutical composition. Carriers used include lactose, white sugar, sodium chloride, glucose, urea, starch, calcium carbonate, kaolin, crystalline cellulose, and silicic acid. Binders used include water, ethanol, propanol, simple syrup, glucose solutions, starch solutions, gelatin solutions, carboxymethyl cellulose, shelac, methyl cellulose, potassium phosphate, and polyvinylpyrrolidone. Disintegrating agents used include dried starch, sodium alginate, agar powder, laminalia powder, sodium hydrogen carbonate, calcium carbonate, fatty acid esters of polyoxyethylene sorbitan, sodium laurylsulfate, monoglyceride of stearic acid, starch, and lactose. Disintegration inhibitors used include white sugar, stearin, coconut butter, and hydrogenated oils. Absorption accelerators used include quaternary ammonium base and sodium laurylsulfate. Wetting agents used include glycerin and starch. Adsorbing agents used include starch, lactose, kaolin, bentonite, and colloidal silicic acid. Lubricants used include purified talc, stearates, boric acid powder, and polyethylene glycol. Tablets can be further coated with commonly known coating materials such as sugar coated tablets, gelatin film coated tablets, tablets coated with enteric coatings, tablets coated with films, double layered tablets, and multi-layered tablets.

When shaping the pharmaceutical composition into pill form, any commonly known excipient used in the art can be used. For example, carriers include lactose, starch, coconut butter, hardened vegetable oils, kaolin, and talc. Binders used include gum arabic powder, tragacanth gum powder, gelatin, ethanol. Disintegrating agents used include agar, and laminalia.

For the purpose of shaping the pharmaceutical composition in the form of suppositories, any commonly known excipient used in the art can be used. For example, excipients include polyethylene glycols, coconut butter, higher alcohols, and esters of higher alcohols, gelatin, and semisynthesized glycerides.

When preparing injectable pharmaceutical compositions, solutions and suspensions are sterilized and are preferably made isotonic to blood. Injection preparations may use carriers commonly known in the art. For example, carriers for injectable preparations include water, ethyl alcohol, propylene glycol, ethoxylated isostearyl alcohol, polyoxylated isostearyl alcohol, and fatty acid esters of polyoxyethylene sorbitan. One of ordinary skill in the art can easily determine with little or no experimentation the amount of sodium chloride, glucose, or glycerin necessary to make the injectable preparation isotonic.

Additional ingredients, such as dissolving agents, buffer agents, and analgesic agents may be added. If necessary, coloring agents, preservatives, perfumes, seasoning agents, sweetening agents, and other medicines may also be added to the desired preparations.

The amount of tadalafil or salt thereof contained in a pharmaceutical composition should be sufficient to treat, ameliorate, or reduce the symptoms associated with male erectile dysfunction. Preferably, tadalafil is present in an amount of about 1% to about 70% by weight, and more preferably from about 1% to about 30% by weight of the dose.

The pharmaceutical compositions of the invention may be administered in a variety of methods depending on the age, sex, and symptoms of the patient. For example, tablets, pills, solutions, suspensions, emulsions, granules and capsules may be orally administered. Injection preparations may be administered individually or mixed with injection transfusions such as glucose solutions and amino acid solutions intravenously. If necessary, the injection preparations may be administered intramuscularly, intracutaneously, subcutaneously or intraperitoneally. Suppositories may be administered into the rectum.

The dosage of a pharmaceutical composition for treating schizophrenia according to the invention will depend on the method of use, the age, sex, and condition of the patient. Preferably, tadalafil is administered in an amount from about 0.1 mg/kg to about 10 mg/kg of body weight/day. More preferably, about 1 mg to 200 mg of tadalafil may be contained in a dose.

The present invention, in certain of its embodiments, is illustrated by the following non-limiting examples.

EXAMPLES

The particle size of tadalafil described herein was measured by Malvern Laser Diffraction using a Mastersizer S instrument. The measuring instrument was equipped with a small cell dispersion unit MS1 with a digital dispersion unit controller. The measurement was performed by using range lens 300RF (working range 0.05-900 mcm), beam length: 2.40 mm, presentation 3$$D (Fraunhofer), number of sweeps 4000, and speed rate 2300±10 rpm. The dilution medium was 0.1% w/v Span 80 in a saturated solution of tadalafil in cyclohexane. The measurement began after 10 seconds of recirculation, after the powder was added directly into the measurement cell filled with the dilution medium. According to the accepted rules of Good Manufacturing Procedures, a sample of tadalafil was measured after a successful blank measurement (% obscuration NMT 0.1%) was performed.

Example 1

Industrial-scale Crystallization of Tadalafil

A 100 liter GL reactor equipped with a mechanical stirrer, condenser, and thermometer was charged with crude tadalafil (4 Kg, calculated on a dry basis), acetone (80 L) and processed water (24 L) to obtain a slurry. The slurry was heated to reflux to obtain a clear solution. The clear solution was then filtered through mechanical filters (5, 1 and 0.2 microns) and the filtrate was transferred to a clean 160 liter GL reactor. Optionally, the filtrate was reheated to reflux and then cooled to 50° C. Then, processed water (48 L) was added over 3.5 hours to the hot filtrate to obtain a suspension that can be seeded to induce precipitation. The obtained suspension was filtered by centrifuge wand.

Alternatively, after adding water, the suspension was heated to 50° C.-65° C. and then cooled to 45° C., followed by stirring at this temperature for 1 hour. The suspension was then reheated to 65° C., and cooled again, to 20° C.-50° C. over 3.5 hours. The precipitate obtained was filtered in a centrifuge wand and washed with water. Final dry material—2.7 Kg with particle size, d(0.9)>60-500 microns (d(0.9) between at least 60 up to about 500 microns).

Example 2

Crystallization of Tadalafil

A 10 liter GL reactor equipped with a mechanical stirrer, condenser, and thermometer was charged with crude tadalafil (250 g, calculated on a dry basis), acetone (6 L) and processed water (1.5 L) to obtain a slurry. The slurry was heated to reflux to obtain a clear solution. The solution was then cooled to 50° C. At 50° C., processed water (3.75 L) was added to the solution over 2.5 hours to obtain a suspension, and the suspension was stirred for an hour. The suspension was filtered by centrifuge wand.

Alternatively, after adding water the suspension was heated to about 50° C.-65° C. and then cooled to 45° C. The suspension was stirred at this temperature for about 1 hour and then reheated to about 65° C. The mixture was then cooled to about 20° C. over 1 hour, filtered in a vacuum filter, and washed with processed water. Final dry material—215 g (dry) with particle size, d(0.9)>about 60 microns (d(0.9)>60-500 microns).

Example 3

Controlling the Particle Size

A 10 mg sample of tadalafil having a particle size of d(0.9) =584 microns was milled using a micronizer (50 mm with 4.0 bar feed air and 3.0 bar milling air). The resulting tadalafil has a particle size, (0.9)=about 228.7 microns.

Example 4

Controlling the Particle Size

A 10 mg sample of tadalafil having a particle size of d(0.9) =584 microns was milled using a micronizer (50 mm with 2.0 bar feed air and 1.0 bar milling air). The resulting tadalafil has a particle size, d(0.9)=about 105.8 microns.

Example 5

Controlling the Particle Size

A 0.9 Kg sample of tadalafil having a particle size of d(0.9)=538.6 microns was milled using a Pin-Mill with 9.6 Kg/hr feed rate and 12,000 rpm milling speed. The resulting tadalafil has a particle size, d(0.9)=about 52.4 microns.

Example 6

Controlling the Particle Size

A 0.9 Kg sample of tadalafil having a particle size of d(0.9)=553.5 microns was milled using a Pin-Mill with 9.6 Kg/hr feed rate and 4500 rpm milling speed. The resulting tadalafil has a particle size, d(0.9)=about 202.7 microns.

What is claimed is:

1. Particulate tadalafil wherein at least 90% of the particles have a particle size of about 200 to about 600 microns.

2. A process of preparing the particulate tadalafil of claim 1 comprising the steps of:
   a) combining tadalafil with a solvent selected from the group consisting of $C_3$-$C_8$ ketones, nitrites, $C_1$-$C_6$ alcohols, water and mixtures thereof, to obtain a slurry;
   b) heating the slurry of step a) to a temperature of about 45° C. to about reflux to obtain a clear solution;
   c) combining the solution of step b) with water to obtain a suspension; and
   d) recovering tadalafil.

3. The process of claim 2 wherein the solvent is selected from the group consisting of acetone, methylisobutyl ketone, methylethyl ketone, acetonitrile, methanol, ethanol, isopropanol, butanol, water and mixtures thereof.

4. The process of claim 2 wherein the solvent is a mixture of a $C_3$-$C_8$ ketone or nitrile with water or a $C_1$-$C_6$ alcohol.

5. The process of claim 4 wherein the $C_3$-$C_8$ ketone or nitrile is present in the mixture in a ratio of about 2:1 to about 10:1 to water or a $C_1$-$C_6$ alcohol.

6. The process of claim 4 wherein the solvent is a mixture of at least one $C_3$-$C_8$ ketone and water.

7. The process of claim 6 wherein the solvent is a mixture of acetone and water.

8. The process of claim 2 wherein the slurry obtained in step a) contains about 2.5% to about 4.5% of tadalafil by volume.

9. The process of claim 2 wherein the slurry obtained in step a) is heated to a temperature of about 45° C. to about 100° C.

10. The process of claim 9 wherein the slurry obtained in step a) is heated to a temperature of about 45° C. to about 65° C.

11. The process of claim 2 wherein the solution of step b) is cooled to a temperature of about 30° C. to about 60° C. prior to combining the solution with water.

12. The process of claim 2 wherein the solution and water are combined portion-wise in step c).

13. The process of claim 12 wherein the solution and water are combined by adding water to the solution in a drop-wise manner.

14. The process of claim 2 wherein the solution is combined with an amount of water equaling about 1 to about 3 times the volume of the solvent used in step a).

15. The process of claim 14 wherein the solution is combined with an amount of water equaling about 2 times the volume of the solvent used in step a).

16. The process of claim 12 wherein the solution and water are combined over a period of about 30 minutes to about 15 hours.

17. The process of claim 16 wherein the solution and water are combined over a period of about 1 hour to about 5 hours.

18. The process of claim 17 wherein the solution and water are combined over a period of about 3.5 hours to about 4 hours.

19. The process of claim 11, further comprising repeating the heating and cooling steps at least once prior to the recovery of tadalafil.

20. The process of claim 19 wherein the suspension is cooled for about 1 hour to about 6.5 hours.

21. The process of claim 20 wherein the suspension is cooled for about 4 hours to about 5 hours.

22. The process of claim 2 wherein the solution obtained in step b) is seeded with tadalafil.

23. A process for controlling the particle size of tadalafil to obtain tadalafil having a desired particle size comprising the steps of:
   a) combining tadalafil with a solvent selected from the group consisting of $C_3$-$C_8$ ketones, nitrites, $C_1$-$C_6$ alcohols, water and mixtures thereof to obtain a slurry; and
   b) milling the tadalafil of step a) to obtain tadalafil having a desired particle size of about 40-100 microns.

24. The process of claim 23 wherein milling is performed by a cone mill.

25. The process of claim 23 wherein the particle size of the product is controlled by at least one of: changing the rotating speed of the impeller, selection of screens with different hole size or using different types of impellers.

26. The process of claim 23 wherein the particle size of the product is controlled by selection of screens with different hole size.

27. A process for controlling the particle size of tadalafil to obtain tadalafil having a desired particle size comprising the steps of:
   a) combining tadalafil with a solvent selected from the group consisting of $C_3$-$C_8$ ketones, nitrites, $C_1$-$C_6$ alcohols, water and mixtures thereof to obtain a slurry;
   b) heating the slurry of step a) to a temperature of about 45° C. to about reflux to obtain a clear solution;
   c) combining the solution of step b) with water to obtain a suspension;
   d) recovering particulate tadalafil wherein at least 90% of the particles have a particle size of about 200 to about 600 microns; and
   e) milling the tadalafil of step d) to obtain tadalafil having a desired particle size of about 40-100 microns.

28. A pharmaceutical composition comprising tadalafil prepared according to claim 2, 23 or 24 and one or more pharmaceutically acceptable excipients, diluents or carriers.

29. A process for preparing a pharmaceutical formulation comprising combining tadalafil prepared according to claim 2, 23 or 24 with a pharmaceutically acceptable carrier.

* * * * *

UNITED STATES PATENT AND TRADEMARK OFFICE
CERTIFICATE OF CORRECTION

PATENT NO. : 7,417,044 B2
APPLICATION NO. : 11/364630
DATED : August 26, 2008
INVENTOR(S) : Orman et al.

It is certified that error appears in the above-identified patent and that said Letters Patent is hereby corrected as shown below:

Claim 2, line 4, change "nitrites" to --nitriles--.

Claim 23, line 5, change "nitrites" to --nitriles--.

Claim 27, line 5, change "nitrites" to --nitriles--.

Signed and Sealed this

Sixteenth Day of February, 2010

David J. Kappos
*Director of the United States Patent and Trademark Office*

UNITED STATES PATENT AND TRADEMARK OFFICE
CERTIFICATE OF CORRECTION

PATENT NO. : 7,417,044 B2  Page 1 of 1
APPLICATION NO. : 11/364630
DATED : August 26, 2008
INVENTOR(S) : Orman et al.

It is certified that error appears in the above-identified patent and that said Letters Patent is hereby corrected as shown below:

Column 8, Claim 2, line 47, change "nitrites" to --nitriles--.

Column 10, Claim 23, line 5, change "nitrites" to --nitriles--.

Column 10, Claim 27, line 22, change "nitrites" to --nitriles--.

This certificate supersedes the Certificate of Correction issued February 16, 2010.

Signed and Sealed this

Twenty-third Day of March, 2010

David J. Kappos
*Director of the United States Patent and Trademark Office*